(12) United States Patent
Van Dijk et al.

(10) Patent No.: US 8,995,733 B2
(45) Date of Patent: Mar. 31, 2015

(54) MICRODISSECTION METHOD AND INFORMATION PROCESSING SYSTEM

(75) Inventors: Erik Martinus H. P. Van Dijk, Eindhoven (NL); Sjoerd Stallinga, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 139 days.

(21) Appl. No.: 13/266,552

(22) PCT Filed: Apr. 20, 2010

(86) PCT No.: PCT/IB2010/051725
§ 371 (c)(1),
(2), (4) Date: Oct. 27, 2011

(87) PCT Pub. No.: WO2010/125495
PCT Pub. Date: Nov. 4, 2010

(65) Prior Publication Data
US 2012/0045790 A1    Feb. 23, 2012

(30) Foreign Application Priority Data
Apr. 28, 2009  (EP) .................................. 09305369

(51) Int. Cl.
G06K 9/00    (2006.01)
G06T 7/00    (2006.01)
(52) U.S. Cl.
CPC ..... *G06T 7/0014* (2013.01); *G06T 2207/10056* (2013.01); *G06T 2207/20104* (2013.01); *G06T 2207/30024* (2013.01)

USPC .......................................................... 382/128
(58) Field of Classification Search
None
See application file for complete search history.

(56) References Cited

U.S. PATENT DOCUMENTS

| 5,526,258 | A  | * | 6/1996 | Bacus ........................... 382/129 |
| 7,148,966 | B2 |   | 12/2006 | Baer |
| 2004/0085443 | A1 |   | 5/2004 | Kallioniemi |
| 2005/0165290 | A1 |   | 7/2005 | Kotsiantl |
| 2006/0166253 | A1 |   | 7/2006 | Kononen |
| 2007/0160280 | A1 |   | 7/2007 | Schutze et al. |
| 2007/0224699 | A1 |   | 9/2007 | Gates |
| 2008/0044849 | A1 |   | 2/2008 | Bocking |
| 2008/0206807 | A1 |   | 8/2008 | Duymelinck |
| 2008/0248478 | A1 |   | 10/2008 | Renzing |
| 2010/0055759 | A1 | * | 3/2010 | Blau et al. ................... 435/173.9 |
| 2010/0215227 | A1 | * | 8/2010 | Grunkin et al. ............... 382/128 |
| 2011/0238325 | A1 | * | 9/2011 | Lett et al. ........................ 702/19 |

FOREIGN PATENT DOCUMENTS

| JP | 2003161893 | 6/2003 |
| WO | 9713838 A1 | 4/1997 |
| WO | 2008080403 A1 | 7/2008 |

* cited by examiner

*Primary Examiner* — Nirav G Patel

(57) ABSTRACT

A method for use in biology, histology, and pathology includes providing a digital first image of a first slice of an object having biological material; generating a digital second image of a second slice of the object; determining a region of interest in the second image based on a region of interest in the first image; determining a region of interest in the second slice based on the region of interest in the second image; and extracting material from the region of interest in the second slice.

18 Claims, 10 Drawing Sheets

FIG. 9
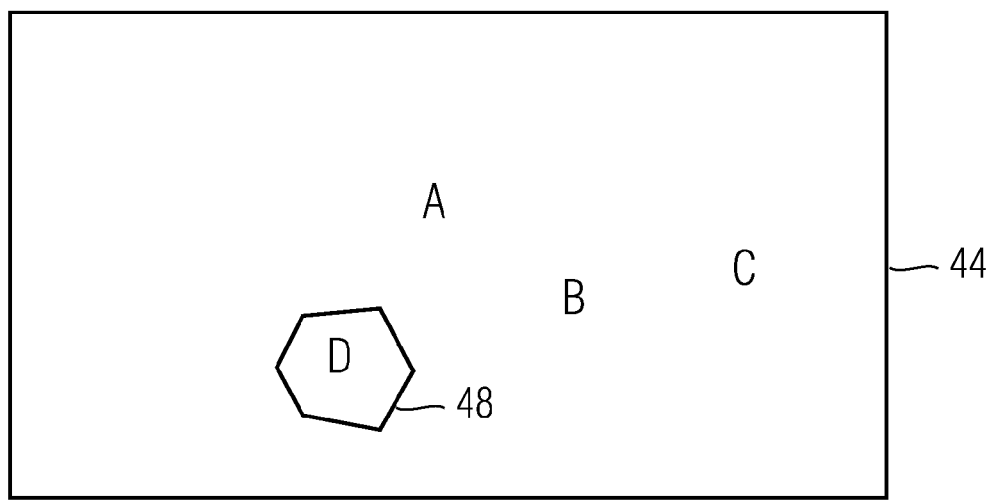
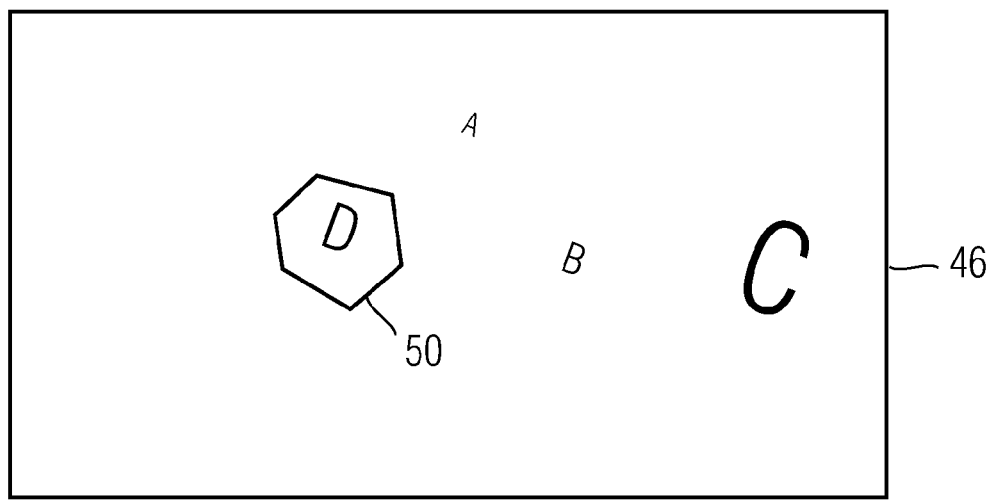
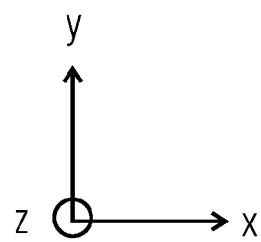

MICRODISSECTION METHOD AND INFORMATION PROCESSING SYSTEM

FIELD OF THE INVENTION

In a first aspect, the invention relates to a method for use in biology, histology and pathology.

In a second aspect, the invention relates to a system for use in biology, histology and pathology.

In a third aspect, the invention relates to a data carrier.

In a fourth aspect, the invention relates to an information processing system for use in biology, histology and pathology.

BACKGROUND OF THE INVENTION

A pathologist has a central role in the diagnostic part of the care cycle. When a tissue sample is taken from a patient during a biopsy, it is usually the pathologist who makes a final diagnosis as to the nature and gravity of the disease (mostly cancer related), by microscopic inspection of the tissue and cells from the biopsy.

A microscope slide containing material from a biopsy is typically prepared in several steps as follows. First, the material is usually placed in formalin for fixation and subsequently processed into a paraffin block from which thin (~5 µm) slices are cut. One of these slices is then placed on a microscope glass substrate after which one or more staining agents are applied such that relevant cell or tissue parts are visible with a microscope. Finally a matching fluid/fixative is added to the slice and a thin (~170 µm) microscope cover slip is placed on top of the tissue such that the slice is completely sealed. This enables long time (>10 years) storage of the slide including the slice. Often it is also compulsory to store the paraffin blocks for at least ten years as well.

Although pathology is currently an analogue profession there is a strong drive to move towards digital pathology in order to improve diagnostic efficiency and quality. Digital pathology refers to digitization of the slide in the lab, to storing the resulting images on a server to allow easy access by the pathologist from his or her workstation, and to sharing the clinically relevant information with peers and other clinicians. Adoption of digital pathology would result in the pathologist handling the slides no longer himself, but instead to work with the digital images and other clinical information for making his or her diagnosis.

Using a suitable dissection technique, for example, microdissection by laser (laser microdissection), one or several small samples can be cut out of a tissue slice and be subjected to further molecular testing such as DNA genotyping or RNA transcript profiling. The preparation of the tissue slides is quite analogous to the case of pathology tissue slides, with the difference that now no cover slip is placed on the tissue in order to enable extraction and collection of the selected tissue samples. Histological examination is done by microscopic inspection leading to a selection of one or several areas of interest. Often this selection is made by the pathologist and marked on the back side of the slide. An operator can then use a focused laser beam for cutting along a line that separates the area of interest and the surrounding tissue. The separated tissue is then collected in a collection basket using an adhesive tape or by catapulting it with a defocused beam, after which the collected tissue is processed further. Currently, laser microdissection systems are mainly used in research labs.

A problem standing in the way of more widespread adoption of laser microdissection in the general pathology practice is the fact that current microdissection systems are not matched with the existing pathology workflow. It is currently not possible to do laser microdissection on samples that are used for normal diagnosis due to the presence of the cover slip on the sample. These normal slides should not be damaged during processing. Furthermore, the pathologist currently has to handle the physical slide to indicate which area should be selected, which leads to more slides to be transported to and from the lab. This mismatch in workflow might further increase with the introduction of digital pathology since the pathologist will then no longer handle any physical slides. There is thus a need for a novel system that integrates microdissection into a digital pathology workflow.

It is an object of the invention to facilitate the combined steps of selecting a region of interest in biological material and extracting material from the region of interest. It is another object of the invention to facilitate controlling a workflow involving at least two slices cut from, e.g., the same paraffin block.

These objects are achieved by the features of the independent claims. Further specifications and preferred embodiments are outlined in the dependent claims.

SUMMARY OF THE INVENTION

The method according to the first aspect comprises:
  providing a digital first image of a first slice of an object comprising biological material;
  generating a digital second image of a second slice of the object;
  determining a region of interest in the second image on the basis of a region of interest in the first image;
  determining a region of interest in the second slice on the basis of the region of interest in the second image; and
  extracting material from the region of interest in the second slice.

By extracting material from the region of interest in the second slice, conclusions may be drawn about material in the region of interest in the first slice, assuming that the first slice and the second slice are sufficiently similar. To this end, it may be advantageous that the first slice and the second slice were adjacent before being cut from the object. Also, cutting the second slice may comprise cutting the second slice parallel to the first slice. The object may comprise or consist of a paraffin block comprising the biological material. Providing the first image may comprise generating the first image. Furthermore, generating the first image may comprise cutting the first slice from the object. Similarly, generating the second image may comprise cutting the second slice from the object. It is also noted that determining the region of interest in the second slice and extracting material from the region of interest in the second slice may be interlaced. In particular, the region of interest in the second slice may be defined a posteriori by extracting material from the second slice on the basis of the region of interest in the second image. In this case, the region of interest in the second slice is the region from which the material has been extracted.

Determining the region of interest in the second image may comprise
  determining a geometrical transformation which maps positions of features in the first image into positions of similar features in the second image; and
  applying the geometrical transformation to the region of interest in the first image.

In this context, the term "feature" refers to any localized optical characteristic in an image, e.g. a spot, a line, or a pattern. A spot may, for example, be due to an agglomeration or increased density of cells in a region of the respective slice. The method may comprise identifying features in the first image and in the second image using a feature detection or pattern recognition method. The geometrical transformation may in particular be a composition of a translation in the image plane, a rotation about an axis perpendicular to the image plane, and a scaling operation. Determining the geometrical transformation may thus involve determining a translation vector, a rotation angle, and scaling factor, the scaling factor indicating a size ratio between the first image and the second image.

Determining the region of interest in the second image may comprise aligning the first image and the second image such that at least some features in the first image project onto similar features in the second image and/or such that a contrast of a superposition of the first image and the second image is maximized. To this end, the method may comprise identifying features in the first image and in the second image using a feature detection or pattern recognition method.

Determining the region of interest in the second slice and extracting material from it may comprise
- determining, on the basis of the region of interest in the second image, a new position of a cutting tool relative to the second slice; and
- moving the cutting tool relative to the second slice to the new position.

The cutting tool may, for example, be a cutter, a scalpel, or a laser beam.

Determining the new position may comprise consulting a look-up table or evaluating a function, the look-up table or the function relating positions in the second image to positions of the cutting tool relative to the second slice, or to information equivalent to positions of the cutting tool relative to the second slice. The look-up table may be a digital look-up table stored in a memory or on a data carrier. Generating the look-up table or modifying the look-up table amounts to a calibration step.

The apparatus or system according to the second aspect of the invention comprises:
- means for providing a digital first image of a first slice of an object comprising biological material;
- means for generating a digital second image of a second slice of the object;
- means for determining a region of interest in the second image on the basis of a region of interest in the first image;
- means for determining a region of interest in the second slice on the basis of the region of interest in the second image; and
- means for extracting material from the region of interest in the second slice.

Thereby means for performing the method according to the first aspect of the invention are provided.

The means for determining the region of interest in the second slice and for extracting material from it may comprise
- a device for providing a cutting tool for cutting material out of the second slice;
- means for determining, on the basis of the region of interest in the second image, a new position of the cutting tool relative to the second slice; and
- means for moving the cutting tool relative to the second slice to the new position.

The cutting tool may, for example, be a cutter, a scalpel, or a laser beam. The device for providing the cutting tool may, for example, be the cutter, the scalpel, or a laser for generating the laser beam.

The means for generating the second image may comprise a microscope objective and the means for extracting material may comprise a laser for generating a laser beam, and the apparatus or system may be configured for transmitting the laser beam to the second slice via the microscope objective. Thus essentially the same light path is provided for imaging the slice and for the laser beam, wherein it is understood that the light of the laser beam and the light from the slice propagate in opposite directions. Errors due to a possible misalignment of the microscope objective may thus be reduced.

The data carrier according to the third aspect of the invention carries instructions for controlling an apparatus or system according to the second aspect to perform the method according to the first aspect. The data carrier may, for example, comprise an optical data carrier such as a CD, a DVD, a flash memory, or a magnetic data carrier such as a hard disk. The data carrier may be a distributed data carrier in the sense that it comprises different physical units. In this case any information stored on the data carrier may be stored in a distributed manner, with different units carrying different pieces of the information.

The information processing system according to the fourth aspect of the invention is configured for
- providing a predefined set of process identifiers;
- providing a set of data records associated with an object comprising biological material, wherein each of the data records comprises: a slice identifier identifying a slice of the object, and a process identifier selected from the set of process identifiers, the process identifier indicating a process to which the slice is intended to be subjected;
- providing a user interface for enabling a user to select a data record from the set of data records.

The information processing system thus facilitates controlling a workflow involving at least two slices cut from, e.g., the same paraffin block. The information processing device may be configured in the described manner by means of both hardware and software, the hardware comprising a memory in which the software has been stored, the software comprising executable instructions for controlling the hardware. The data records may be represented in digital (e.g. binary) form in the memory. More particularly, the slice identifiers and/or the process identifiers may be digital representations of alphanumerical constants. The set of data records may comprise a first data record and a second data record, wherein the process identifier in the first data record and the process identifier in the second data record differ. The user interface may be configured for displaying contents of the selected data record. The user interface may further enable the user to modify the data records in the set of data records and/or to add new data records to the set of data records, and/or to remove data records from the set of data records. The information processing system may comprise a computer, e.g. a personal computer, or a computer network. The information processing system may comprise input means and output means. The input and output means may comprise, for example, at least one of the following: a keyboard, a mouse, a trackball, voice recognition means, a monitor such as a liquid crystal display, and sound output means. The input means and the output means may be integrated in the processing system or form distinct units operatively coupled to the information processing system. The user interface may be implemented by software for controlling the input means and the output means such that the user may exchange information with the information processing system. The information processing system may comprise a memory carrying the set of process identifiers, the set of data records, and the software for controlling the user interface. The memory is not necessarily provided by a single physical unit, but may comprise several distinct memories. A distinct memory may be provided by, for example, a magnetic data carrier, such as a hard disk, or an optical data carrier such as a Compact Disk (CD), Digital Versatile Disk (DVD), or a flash memory.

The set of process identifiers may comprise a process identifier identifying a process selected from the following list of processes related to a slice:
   doing nothing with the slice;
   archiving the slice;
   disposing of the slice;
   generating an image of the slice;
   containing the slice in a microscope slide or cartridge;
   sending the slice to another laboratory;
   extracting material from the slice;
   freezing the slice;
   heating the slice;
   sealing the slice;
   marking a region of interest on the slice;
   staining the slice;
   staining the slice by a first staining method;
   staining the slice by a second staining method;
   defining a colour transformation between two staining methods.
The process may be assigned a verbal and/or graphical label. The information processing system may be configured for displaying the label on a monitor. The process identifiers may be used for automated or manual processing of a slice of the object.

The set of data records may indicate, for at least some of the slices indicated by the slice identifiers, an order corresponding to the order in which the at least some slices were arranged before being cut from the object. For example, a number could be included in each or at least some of the data records such that the first slice that was cut from the object is numbered 1, the next slice that was cut is numbered 2, and so on. This may help finding data records relating to adjacent slices. These numbers, together with information about a thickness of each of the adjacent slices, could also be used for generating a three-dimensional image of the object. The number relating to a particular slice and indicating the place previously occupied by the slice in the object may be integrated in the slice identifier or form another entry of the data record. Additionally or alternatively, a data record may contain an entry pointing to another data record, e.g. to the data record of an adjacent slice. Also, information indicating a pair of slices could be added to the data records. This may be useful in order to specify a pair of slices that is intended to be used for defining a colour transformation between colours associated with a first staining method and with a second staining method, respectively. An example of a colour transformation method has been presented by the applicant in a previous application. A pair of slices may, for example, be indicated by a first pointer in a first data record, the first pointer pointing to a second data record, and/or by a second pointer in the second data record, the second pointer pointing to the first data record.

The user interface may be configured for enabling the user to modify the process identifier in the selected data record, by selecting another process identifier from the set of process identifiers. To this end, the user interface may be configured for displaying a list of the process identifiers and/or a list of process labels corresponding to the process identifiers.

A first data record in the set of data records may comprise a first image or a first image identifier, the first image being a digital image of the slice identified by the slice identifier in the first data record, and the first image identifier identifying the first image. Analogously, a second data record in the set of data records may comprise a second image or a second image identifier, the second image being a digital image of the slice identified by the slice identifier in the second data record, and the second image identifier identifying the second image. According to a preferred embodiment, the corresponding slices were cut from the object in parallel cuts. The information processing system may be configured for overlaying the first image and the second image such that features in the first image project onto corresponding features in the second image, to determine a translation and/or rotation and/or size ratio between the first image and the second image. Thus a mapping between points or pixels in the first image and corresponding points or pixels in the second image can be expressed in a simple manner, using a translation vector and an angle of rotation. Furthermore, the information processing system may be configured for determining a region of interest in the second image on the basis of a region of interest in the first image. The information processing system may also be configured for displaying simultaneously the first image and the second image, and for indicating in each of the two images the corresponding region of interest.

In this context, the first data record may comprise information indicating a region of interest in the first image, the region of interest having been defined by a user and the information having being recorded for being transferred to a laboratory in order to prepare a second slice of the object, e.g. for microdissection.

Furthermore, the information processing system may be configured for determining a region of interest to be cut from the second slice, by overlaying the first image and a digital second image of the second slice and projecting the region of interest defined in the first image onto the second image. Thus corresponding regions of interest in corresponding images may be determined in an efficient manner.

The user interface may be configured for enabling the user to add a laboratory identifier selected from a set of laboratory identifiers to the selected data record, and to transmit the selected data record or selected components thereof to a laboratory identified by the selected laboratory identifier. For example, a pathologist working at first laboratory is thus enabled to send a data record of a first slice to a second laboratory equipped with a microdissection facility. The pathologist may include in the data record a digital image of the first slice and a region of interest defined in that digital image. At the second laboratory, a second slice similar to the first slice may then be cut, and a region of interest corresponding to the region of interest in the digital image of the first slice may be determined as described with reference to the first and second aspects of the invention.

The user interface may also be configured for enabling the pathologist to ask a laboratory to cut two slices from an object comprising biological material, e.g. from a paraffin block, and to generate digital images of the two slices.

In a related aspect, a method comprises the steps of
   receiving a block comprising the biological material;
   cutting, in a first cut, a first slice from the block;
   cutting, in a second cut parallel to the first cut, a second slice from the block;
   placing the first slice on a first substrate;
   placing the second slice on a second substrate;
   placing a cover slide on the first slice;
   not covering the second slice;
   extracting material from the second slice.
Thus two microscope slides are prepared, namely, a first microscope slide comprising the first substrate, the first slice, and the cover slide, and a second microscope slide comprising the second substrate and the second slice. The first microscope slide and the second microscope slide are also referred to in this application as the standard slide and the dissection slide, respectively. Different slides may thus be used for diagnosis and for microdissection. The block may in particular be a paraffin block. The biological material may comprise, for example, tissue, individual cells such as blood cells or bacteria, or fungi. The first slice and the second slice are preferably prepared from nearby cuts from the block so that they can be expected to have similar morphologies.

The second cut may in particular be adjacent to the first cut. It may then be expected that the first slice and the second slice have a very similar morphology.

The material to be extracted may, for example, be extracted by laser microdissection. Alternatively it may, for example, be extracted mechanically, e.g. by using a fine scalpel.

The method may further comprise generating a digital image of the first slice, the image being a first image, and generating a digital image of the second slice, the image being a second image.

The method may further comprise recording information indicating that the first slice is intended for imaging and/or for conservation; and recording information indicating that the second slice is intended for microdissection.

The method may further comprise the successive steps of:
defining a region of interest in the first image;
determining from the region of interest in the first image a region of interest in the second image; and
determining from the region of interest in the second image a region of interest in the second slice.

The region of interest in the second slice may thus be derived from the region of interest in the first image. Alternatively a region of interest could be defined directly in the second image and from it the corresponding region of interest in the second slice can be determined. However, the first slice being covered by a cover slip, it may be expected that, depending on the equipment used, the first slice can be imaged more conveniently and possibly more accurately. There may also be situations in which the second slice is produced only after the first slice has been examined and the region of interest has been defined.

Determining the region of interest in the second image may comprise overlaying the first image and the second image so as to match features in the first image to corresponding features in the second image. Corresponding features in the two images may be identified automatically, for example, using a pattern recognition algorithm. Such features may, for example, be cells, structures of cells, or agglomerations of cells. The purpose of this so-called registration of two images is to determine the part of the second slice that needs to be cut out. For reasons of liability, quality assurance and approval by healthcare authorities it may be necessary that a pathologist approves explicitly the outcome of the registration. Thus a human intervention may be part of the method.

The method may further comprise transmitting the first image from a computer to a dissection unit. The dissection unit may then generate the second image from the second slice in real time and simultaneously overlay the first image to the second image thus generated. Errors due to a misalignment or motion of the second slice relative to the dissection unit may be minimized.

In yet another related aspect, a system is configured for receiving a block comprising the biological material;
cutting, in a first cut, a first slice from the block;
cutting, in a second cut parallel to the first cut, a second slice from the block;
placing the first slice on a first substrate;
placing the second slice on a second substrate;
placing a cover slide on the first slice;
not covering the second slice; and
extracting material from the second slice.

The system may comprise:
a computer for defining a region of interest in a digital image of the first slice or of the second slice;
a dissection unit for receiving from the computer the digital image along with digital information about the region of interest and for determining from the digital image and the digital information a corresponding region of interest in the second slice and for extracting material from the region of interest in the second slice.

The system may be an integrated workflow system. The system may be fully automated. Alternatively, some of the functions of the system may, at least optionally, be fulfilled by a human. Thus a human, or more than one human, for example, one or more pathologists or laboratory assistants, may be part of the system. The system may use a database system for storing and retrieving images by multiple parties (e.g. pathologist and lab), and a workstation with software for viewing these images and for selecting regions of interest (e.g. automatically or by the pathologist). The information on the selected regions of interest can be stored in the database system or be sent directly to a lab where a dissection slide can be prepared from an adjacent cut from the block comprising the biological material. The dissection unit may comprise an imaging system for taking an image of the dissection slide to generate the second image, and an information processing device for overlaying the first image (obtained from the dissection slide), and the second image (obtained from the standard slide) so as to identify the regions of interest on the dissection slide. This enables the dissection unit to cut out and collect the correct regions. The dissection unit may in particular be a laser microdissection unit. It is pointed out that the system may comprise a plurality of machines or apparatuses which are not necessarily physically coupled to each other.

BRIEF DESCRIPTION OF THE DRAWINGS

FIG. 9 schematically illustrates an example of a digital first image and an example of a digital second image.

DETAILED DESCRIPTION OF THE INVENTION

Figure 1:
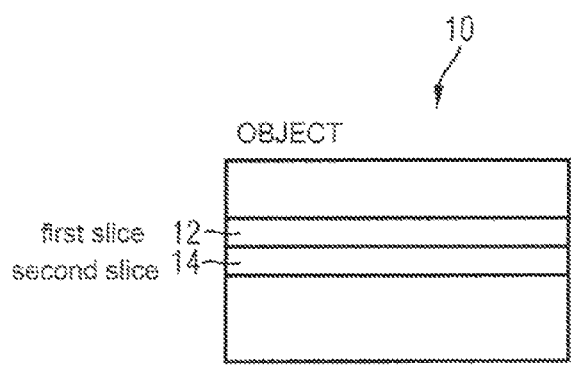
FIG. 1 is a schematic side view of a paraffin block containing biological material.

Unless specified otherwise, identical or similar reference numerals appearing in different Figures label identical or similar components.

Shown in FIG. 1 is a schematic side view of a paraffin block 10 comprising biological material, for example, one or more tissue samples, or individual cells. The block 10 comprises a first layer 12 and an adjacent second layer 14 which are destined to be cut from the block to form a first slice 12 and second slice 14, respectively. The first layer 12 and the second layer 14 may alternatively be non-adjacent layers of the block 10 separated by a distance sufficiently short for the two layers 12, 14 to have similar features. More precisely, the two layers 12, 14 are sufficiently near each other for a feature of interest in the block 10 to extend through both layers 12, 14. It is noted that the layers 12, 14 are merely conceptual. They do not need to be defined by any morphological features of the block; rather, they are defined a posteriori by cutting them from the block 10. It should also be noted that there may be a significant delay (for example, several days, weeks, months, possibly even years) between cutting the first slice 12 and cutting the second slice 14.

Figure 2:
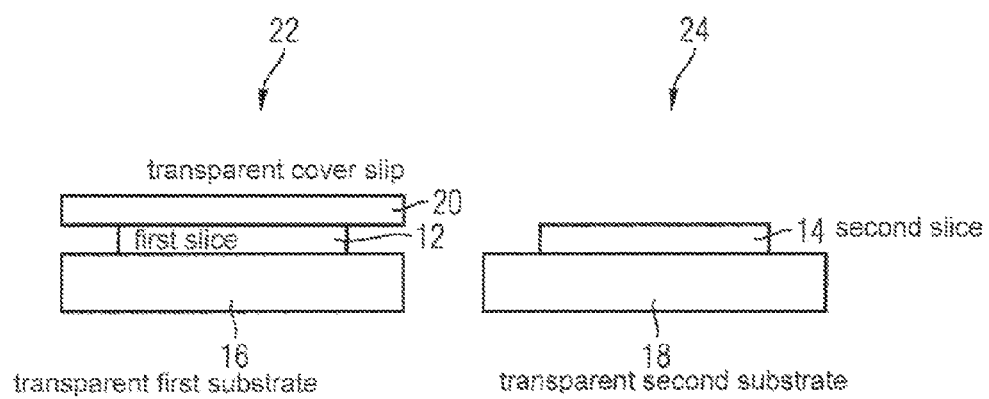
FIG. 2 is a schematic side view of a first microscope slide and a second microscope slide.

Referring now to FIG. 2, there is shown a pair of microscope slides 22, 24. The pair 22, 24 comprises a first microscope slide 22 (standard slide) and a second microscope slide 24 (dissection slide). The standard slide comprises a transparent first substrate 16 carrying the first slice 12 described above with reference to FIG. 1, and a transparent cover slip 20. A matching liquid (not shown) may also be contained between the substrate 16 and the cover slip 20. The dissection slide 24 comprises a transparent second substrate 18 carrying the second slice 14 described above with reference to FIG. 1. In contrast to the standard slide 24, the dissection slide 26 does not comprise any element that could obstruct access to the second slice 14 from above. In particular, it comprises no cover slip. The standard slide 22 is intended for being investigated under a microscope and/or for being conserved over a minimum period of e.g. one month or one year, whereas the dissection slide 24 is intended to be used for taking a sample from the second slice 14, for example, by cutting out the sample from the second slice 14 using a dissection technique, for example, laser microdissection.

Figure 3:
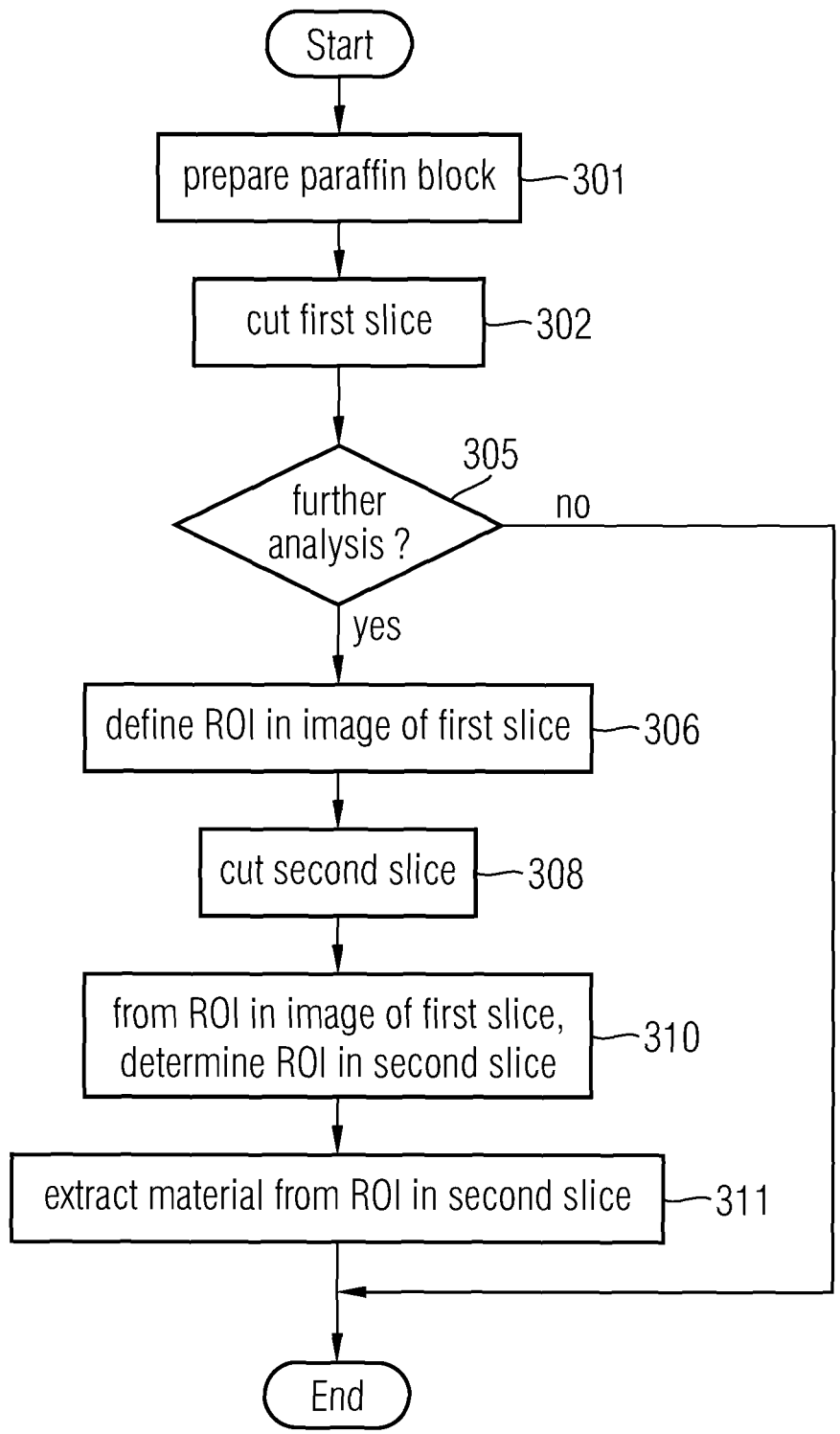
FIG. 3 is a flow chart of a first dissection method.

FIG. 3 illustrates an example of method for use in pathology and histology. In a first step 301, a paraffin block comprising biological material is prepared. This can be done by any method known in the art. A first slice is cut from the block (step 302) in a first cut, using e.g. a microtome. The first slice may be mounted on a transparent substrate, stained and covered by a cover slip, to form a standard slide, which may be imaged by means of a microscope. The microscope may, for example, provide a brightfield imaging mode, and/or a dark field imaging mode, or a confocal scanning imaging mode. A pathologist or a computer then analyzes an image of the first slice. The computer may be equipped with pattern recognition software. Based on the image of the first slice, it is then decided (step 305) whether a further, more detailed analysis is to be made. If so, a region of interest is defined in the image of the first slice (step 306), and a second slice is cut from the paraffin block in a cut parallel, preferably adjacent, to the first cut (step 308). Optionally this second slice can be stained before it is imaged, using the same stain as used to make the standard slide, or using a different stain. By overlaying an image of the first slice and an image of the second slice, the region of interest defined in the image of the first slice is projected onto the second slice, to define a corresponding region of interest in the second slice (step 310). Step 310 may involve placing the second slice in a dissection unit that is configured for taking an image of the second slice and for overlaying that image (second image) and the image of the first slice (first image) to determine from the region of interest in the first image the corresponding region of interest in the second slice. The dissection unit may comprise a computer for controlling these steps. Once the region of interest in the second slice has been determined, it is cut out of the second slice (step 311). It is then passed on to a different station for further analysis. If in step 305 it is decided that no further analysis is required, the process comes to an end.

Figure 4:
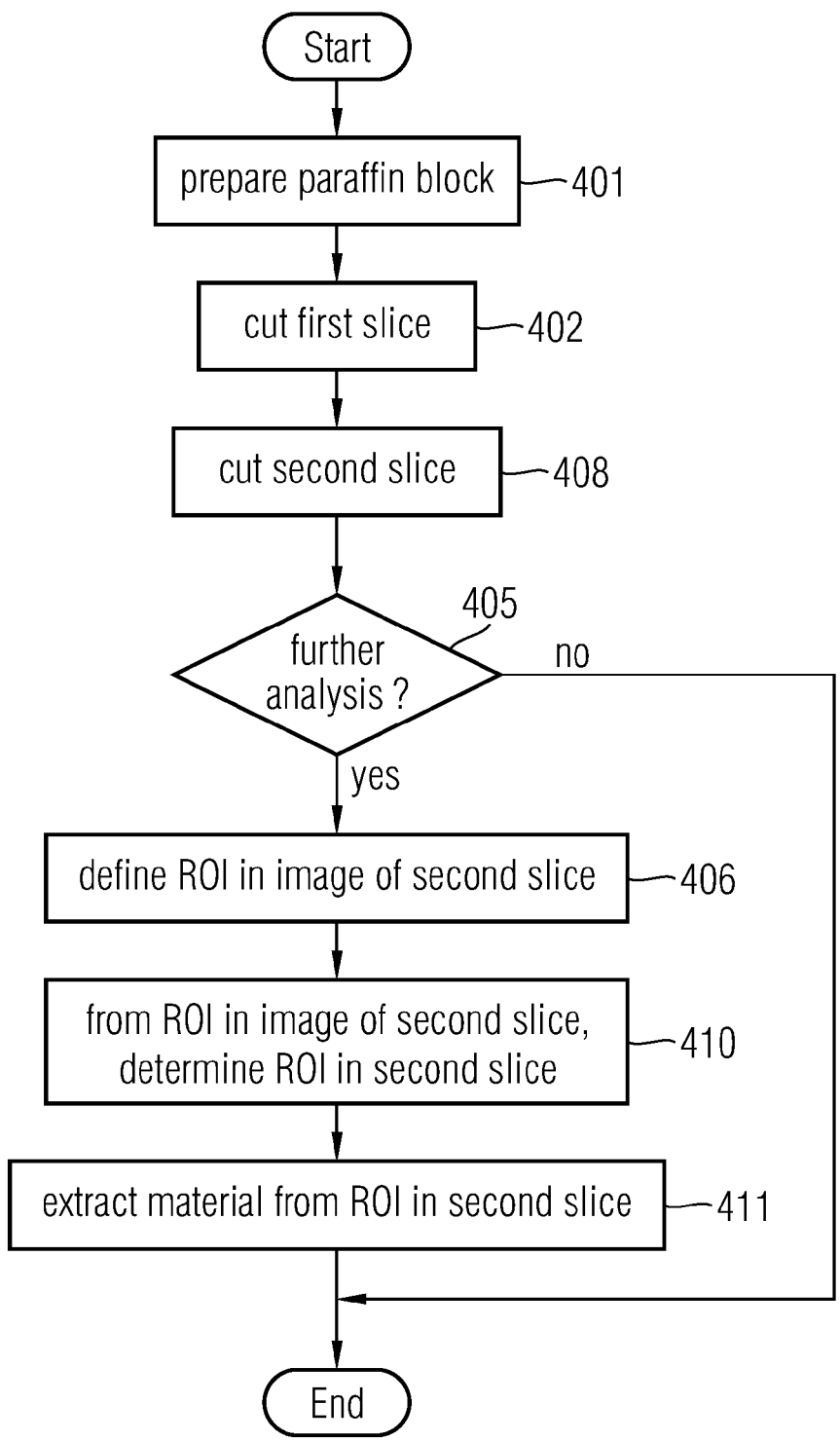
FIG. 4 is a flow chart of a second dissection method.

Turning to FIG. 4, there is illustrated a variant of the method described above with reference to FIG. 3. Steps 401 to 411 are analogous, respectively, to steps 301 to 311 of the method discussed with reference to FIG. 3. The present method however differs in that the second slice is prepared along with the first slide (steps 402 and 408) before deciding (step 405) whether or not a further analysis of the biological material is to be performed.

Figure 5:
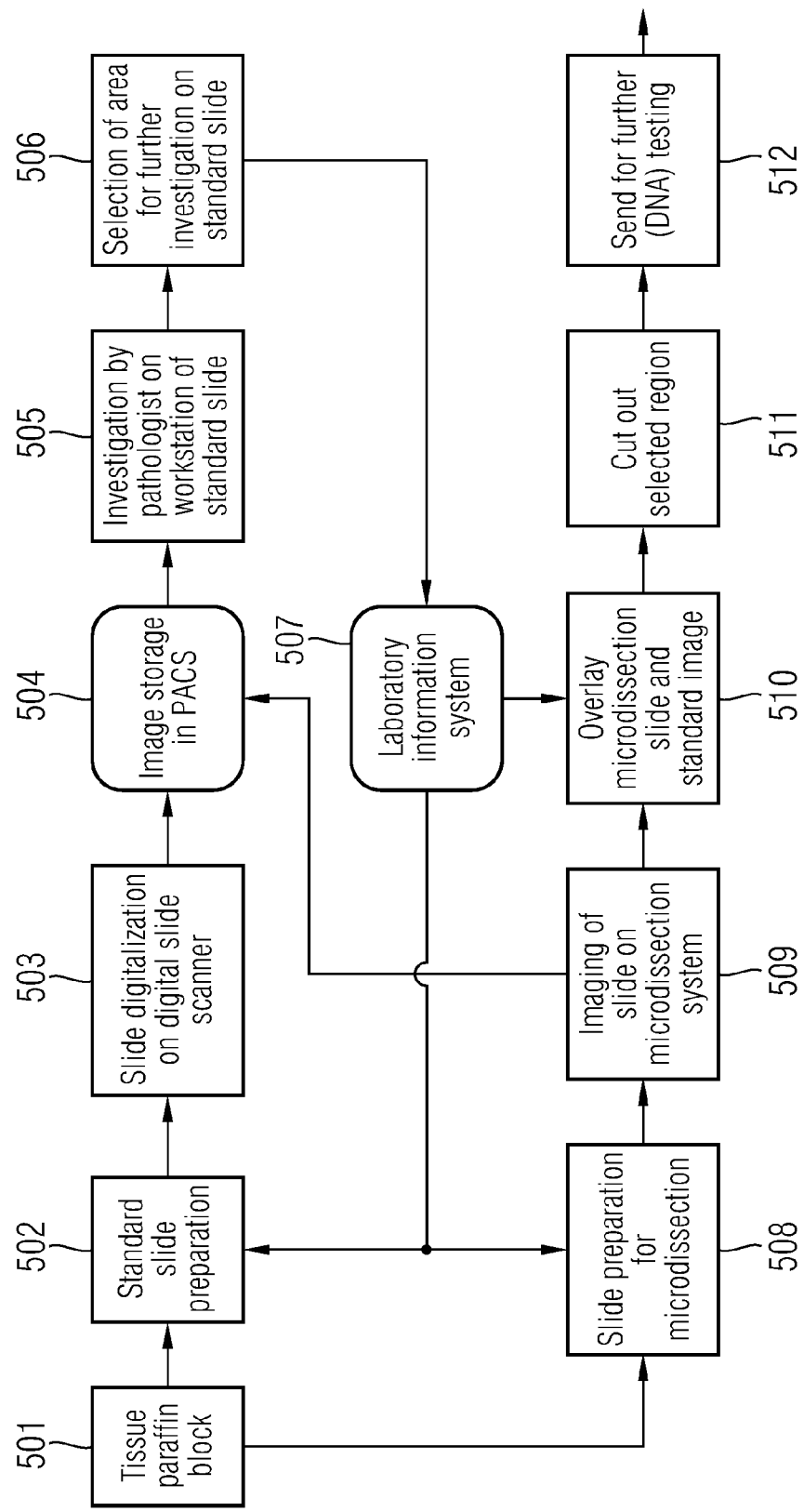
FIG. 5 schematically illustrates a first workflow.

FIG. 5 illustrates an example of a possible workflow. In a laboratory (lab), a paraffin block (501) is prepared or received from another lab. A number of standard slides are prepared (502) from slices cut from the paraffin block. The standard slides are digitized (503) and their digital images are stored (504) in a Picture Archiving and Communication System (PACS). A workstation operating automatically or operated by, for example, a pathologist, retrieves at least one of the digital images from the PACS and displays it on a screen, enabling the pathologist to make a diagnosis. In case the pathologist requires further tests (e.g. DNA tests) on parts of the sample, he selects a region of interest on the screen, corresponding to a region of interest in the digital image of the standard slide. The workstation sends (506) information indicating the region of interest, along with information indicating the requested type of test, to a Laboratory Information System (507). Based on information retrieved from the Laboratory Information System, a new slice is cut from the paraffin block in the lab, preferably adjacent to the cut that was used to prepare the standard slide. The new slice is processed (508) to form a dissection slide and placed in a microdissection apparatus. The microdissection apparatus generates (509) a digital microscopic image of the dissection slide. The digital image of the standard slide and the digital image of the dissection slide are overlayed (510) using feature recognition software, to determine a region of interest on the dissection slide that agrees with the region of interest in the digital image of the standard slide as identified earlier. An image of the region of interest in the dissection slide is then optionally stored for future reference. The microdissection apparatus then cuts out (511) the material in the region of interest in the dissection slide. The material that has been cut out is further analyzed (512).

Figure 6:
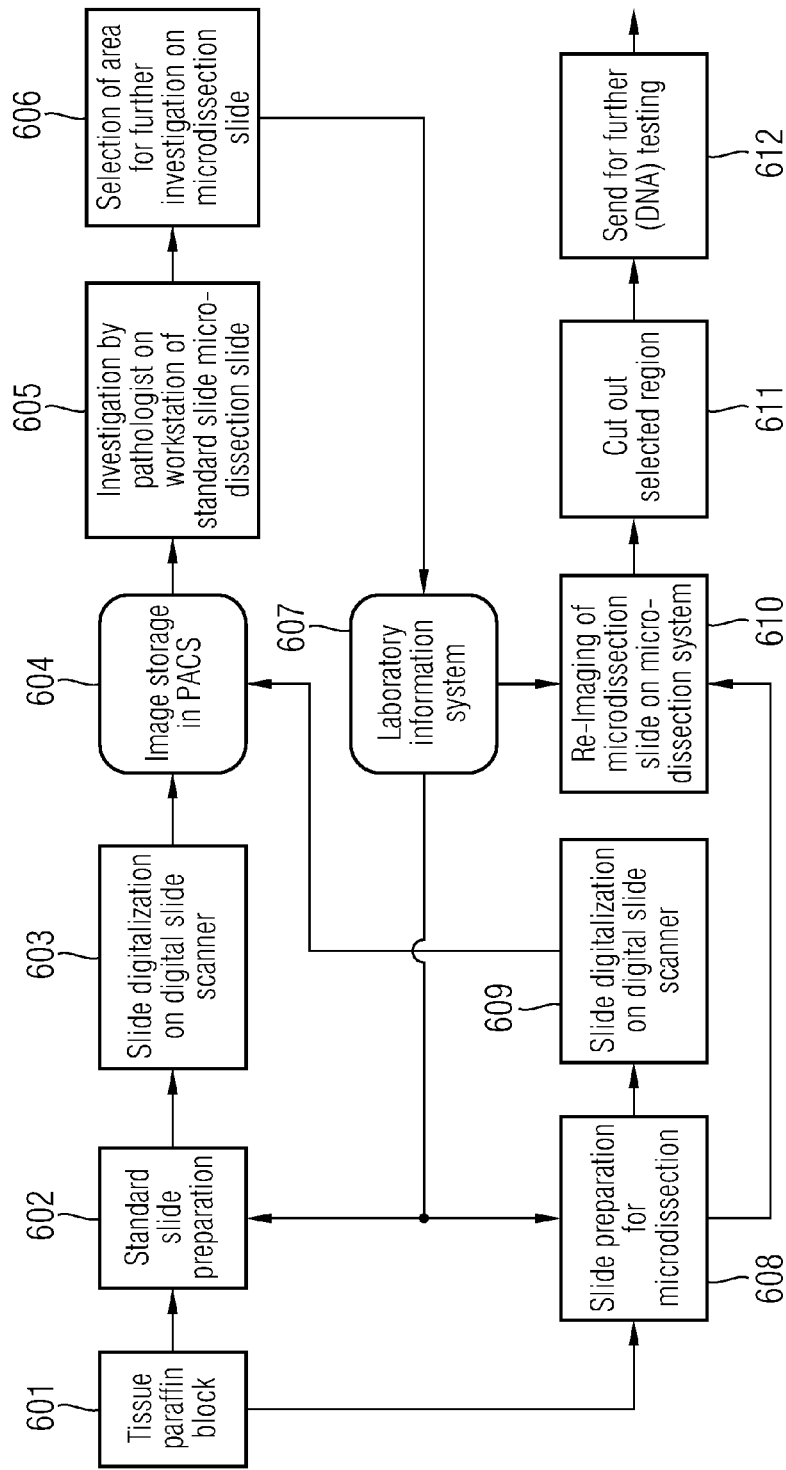
FIG. 6 schematically illustrates a second workflow.

FIG. 6 illustrates another possible workflow. A standard slide and a dissection slide are prepared (602, 608) from the paraffin block before the standard slide is examined. Digital images of both slides are generated (603, 604) and stored in the PACS (607). The pathologist can now directly use these images to indicate an area for further testing (region of interest). This information is again sent to the laser microdissection system (610) where the region of interest in the dissection slide is deduced from the region of interest indicated either in the image of the standard slide or in the image of the dissection slide. This can be done by means of an accurate stage or by image recognition. The microdissection system then cuts (611) the thus determined region out of the dissection slide.

Figure 7:
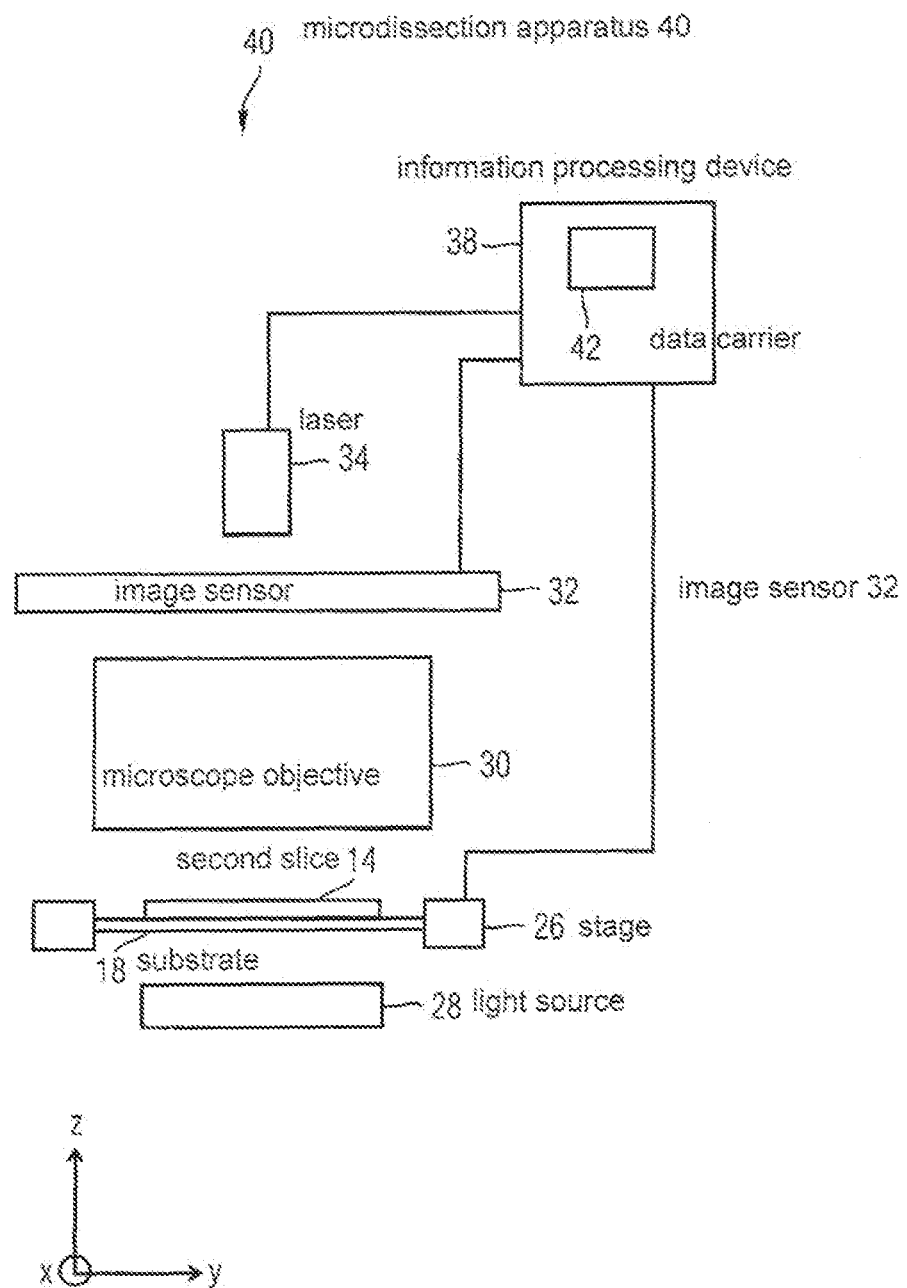
FIG. 7 schematically illustrates an example of a laser microdissection apparatus in a first operational phase.
Figure 8:
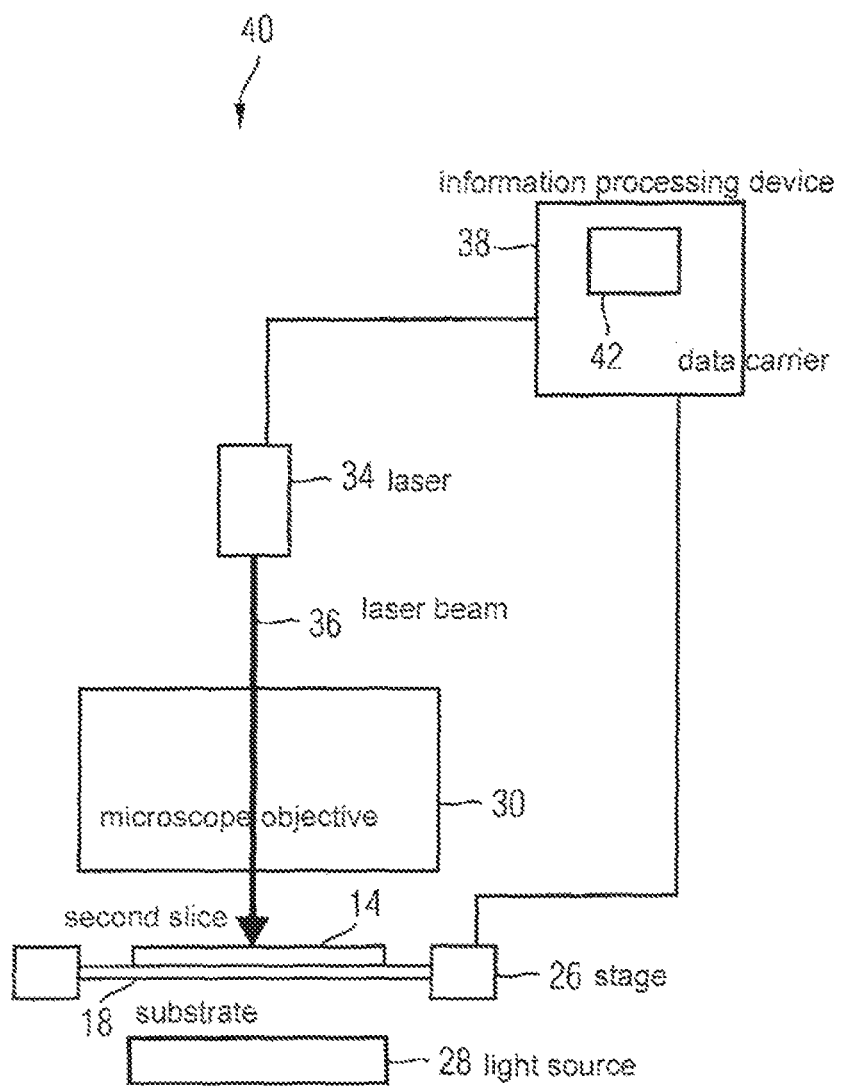
FIG. 8 schematically illustrates the laser microdissection apparatus shown in FIG. 7 in a second operational phase.

Schematically represented in FIGS. 7 and 8 is a microdissection apparatus 40 comprising a light source 28, a stage 26, a microscope objective 30, an image sensor 32, a laser 34, and an information processing device 38. In the example shown, the information processing device 38 is a personal computer (PC) comprising a data carrier 42. The PC 38 is operatively coupled (as represented by the continuous lines) to the stage 26, the image sensor 32, and the laser 34. The data carrier 42 carries instructions for controlling the apparatus 40 to operate as described in the following.

A thin slice 14 (second slice) cut from an object comprising biological material, e.g. from a paraffin block, is placed on a transparent substrate 18, e.g. a glass slide. The substrate 18 is held by the stage 26. In a preparative first operational phase, represented in FIG. 7, the light source 28, e.g. a lamp for emitting white light, evenly illuminates the slice 14 via the transparent substrate 18. At least a portion of the slice 14 is within the field of view of the microscope objective 30. The microscope objective 30 collects light from the slice 14 and generates an optical image of the slice 14, or an optical image of a portion of the slice 14, on the image sensor 32. In this context, and throughout the application, an "image of a slice" may also refer to an image of a portion of the respective slice. The image sensor 32 may, for example, be a pixelated photosensor, e.g. a pixelated photosensor provided by a charge-coupled device (CCD). The photosensor 32 generates an output signal indicative of the intensity and colour distribution of the optical image of the slice 14. The output signal is delivered to the PC 38. On the basis of the output signal, the PC 38 generates a digital image of the slice 14. The position of each pixel of the digital image of the slice 14 is related to a corresponding xy position on the slice 14 relative to the microscope objective 30. Recorded on the data carrier 42 is a digital image of a first slice 12 (see FIG. 1) that was cut parallel to the second slice 14 from the same paraffin block. The digital image of the first slice 12 and the digital image of the second slice 14 are referred to as the first image and the second image, respectively. Also recorded on the data carrier 42, along with the first image, is a region of interest defined in the first image. The first image and the region of interest defined therein may have been received from another information processing device (not shown) used by a pathologist. Using the other information processing device, the pathologist may have defined the region of interest in the first image. From the first image and the region of interest defined therein, the PC 38 determines a corresponding region of interest in the second image. Schematic representations of the first image, the second image, and the regions of interest defined therein, are provided, by way of example, in FIG. 9. Pixels in the region of interest in the second image directly correspond to xy positions in a corresponding region of interest on the second slice 14 on the substrate 18.

In a subsequent second operational phase, represented in FIG. 8, the image sensor 32 is displaced so as to allow the laser 34 to transmit a laser beam 36 through the microscope objective 36 onto the slice 14. In an alternative embodiment (not shown), the image sensor 32 is not displaced, and the laser beam 36 is guided into the microscope objective 30 by means of a beam splitter arranged between the microscope objective 30 and the laser 34. In both embodiments, the focus of the laser beam 36 (indicated by the tip of the arrow 36 in the Figure) is fixed relative to the microscope objective 30. The xy coordinates which characterize positions in an image plane of the microscope objective 30 are chosen such that the focus of the laser beam 36 has fixed coordinates xF and yF, e.g. xF=0 and yF=0. The coordinates xF and yF correspond to a known first pixel in the second image. Said first pixel thus corresponds to the position of the focus of the laser beam 36 on the slice 14 as long as the slice 14 is maintained in its original position in which the second image was taken. The PC 38 then selects a second pixel in the second image, said second pixel being on a line that separates the region of interest from the rest of the second image. In other words, the second pixel is on the border between the region of interest and an adjacent region. The PC 38 then determines a displacement vector pointing from the selected second pixel to the first pixel (the latter pixel still corresponding to the current position of the focus of the laser beam 36 relative to the slice 14). From the displacement vector, the PC 38 determines, e.g. by means of a look-up table, a corresponding displacement vector for the stage 26 and displaces the stage 26 by the displacement vector thus determined. Thus the focus of the laser beam 36 is brought to a point of the second slice which corresponds to the second pixel in the second image. Up to now, the laser 34 may have been inactive (switched off), in which case the laser beam and its focus are understood to be merely conceptual/hypothetical up to now. If the laser beam 36 was inactive, it is now switched on. From the second image, of which it is recalled that its pixels correspond to xy positions relative to the focus of the laser beam 36, and from the region of interest defined therein, and using the look-up table, the PC 38 determines xy displacements of the stage 28 such that a resulting trajectory of the focus of the laser beam 36 on the slice 14 corresponds to a closed line that separates the region of interest in the second image from the adjacent region in the second image. The laser beam 36 thus cuts out a piece of material from the slice 14. The piece that is cut out corresponds to the region of interest in the second image. Consequently, the piece that is cut out also corresponds to the region of interest in the first image. The piece that is cut out can be removed from the slice 14 by any method known in the art, or by any other suitable method, e.g. by catapulting it from the slice 14 using a laser pulse (from the laser 36 or from another laser), or by using adhesive tape.

Many variations of the setup described above with reference to FIGS. 7 and 8 are conceivable without departing from the spirit of the invention. For example, the laser beam 36 might alternatively be applied to the slice 14 via the transparent substrate 18 rather than via the microscope objective 36. This could allow observing the cutting process via the microscope objective 36 and/or catapulting the piece which is cut out of the slice 14 by means of the same laser beam 36.

Referring now to FIG. 9, there are shown, by way of example, schematic representations of a first image 44 and a second image 46 as described above with reference to FIGS. 7 and 8. The first image 44 and the second image 46 were obtained from parallel slices of a paraffin block containing biological material, e.g. tissue or individual cells. Therefore the first image 44 and the second image 46 are similar. Features A, B, C, and D (e.g. agglomerations of cells) are visible in both images. The features A, B, C, and D in the second image 46 somewhat differ in size as compared to their counterparts A, B, C, and D in the first image 44. Furthermore, the second image 46 is rotated by about 20° relative to the first image 44. Also shown in FIG. 9 are a region of interest 48 defined in the first image 44 and a corresponding region of interest 50 determined in the second image 46 from the region of interest 48 in the first image 44. According to one embodiment, the region of interest 50 in the second image 46 is determined by using a geometrical transformation which maps positions of the features A, B, C, D in the first image 44 into positions of the similar features A, B, C, D in the second image 46, and by applying the geometrical transformation thus determined to the region of interest 48 in the first image. According to another embodiment, the region of interest 50 in the second image is determined by aligning the first image 44 and the second image 46 such that at least some features, e.g. A, B, and C, in the first image project onto similar features, e.g. A, B, and C, in the second image. Alternatively, the region of interest 50 in the second image may be determined by maximizing a contrast of a superposition of the first image 44 and the second image 46.

Figure 10:
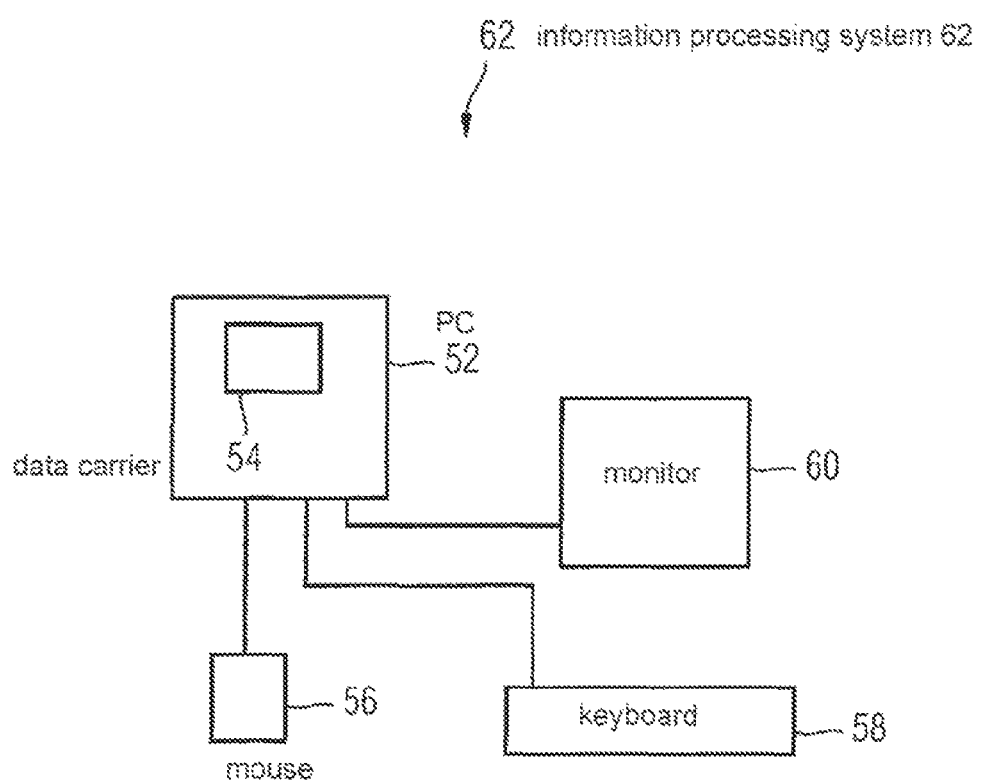
FIG. 10 schematically illustrates an example of an information processing system.

Referring now to FIG. 10, there is illustrated an example of an information processing system 62 according to the fourth aspect of the invention. In the example shown, the information processing system 62 comprises a PC 52 comprising a data carrier 54, e.g. a magnetic disk or an optical storage device or any other suitable memory, a monitor 60, e.g. a liquid crystal display (LCD) 60, a keyboard 58, and a mouse or trackball 56. The data carrier 54 may be provided by more than one distinct physical unit. The data carrier 54 carries instructions for controlling the PC 52, in particular instructions for providing a user interface, for enabling a user (not shown) to enter data into the system 62 via the keyboard and/or the mouse or trackball 56, and to receive data via the monitor 60. The information processing system 62 may comprise further input means and/or output means, e.g. sound input/output means. Furthermore, it may comprise more than one computer. For example, the information processing system 62 could be provided by a computer network.

Figure 11:
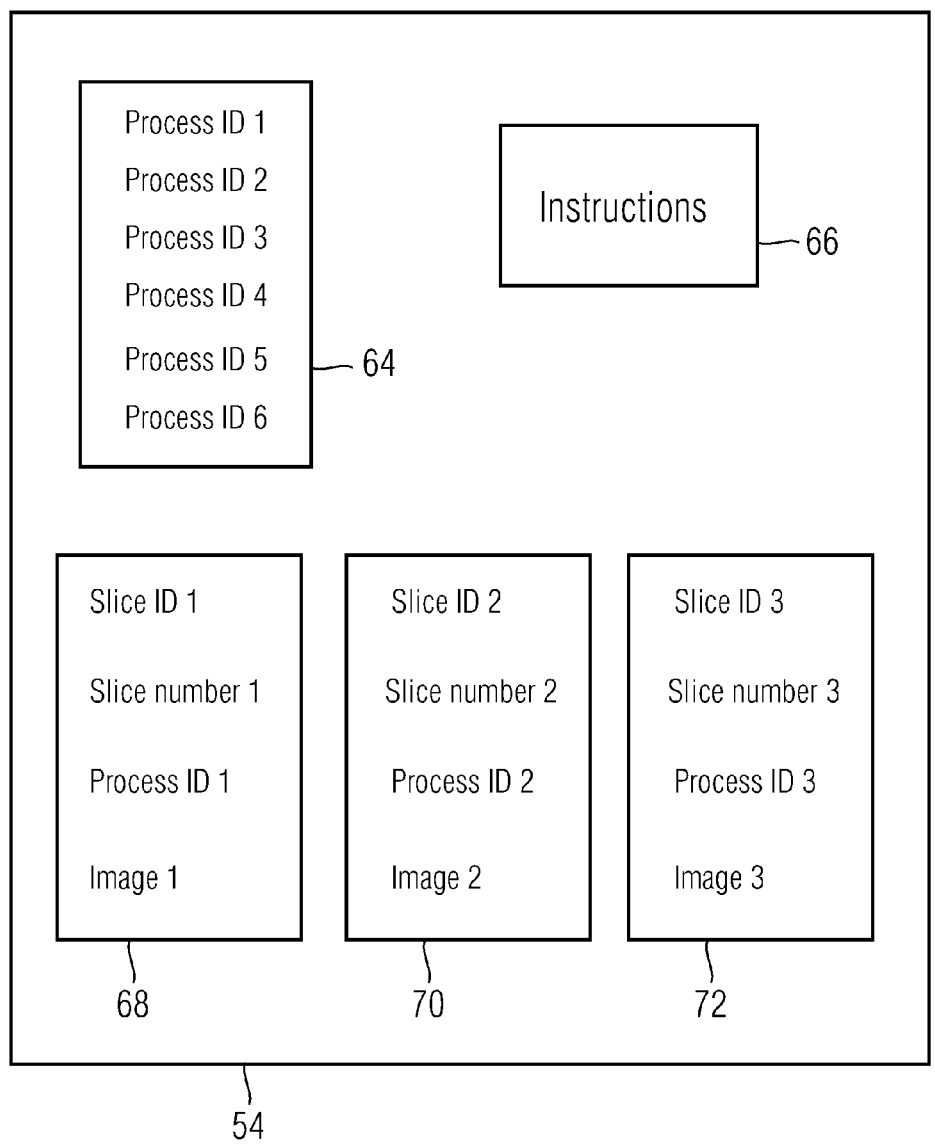
FIG. 11 schematically illustrates information recorded on a data carrier for being read by the information processing system shown in FIG. 10.

The data carrier 54 of the information processing system 62 is schematically illustrated in FIG. 11. Recorded on the data carrier 62 is a predefined set of process identifiers 64, and a set of data records 68, 70, 72 associated with the object 10 (represented in FIG. 1) comprising biological material. The data carrier 54 further carries instructions 66 for controlling the information processing system 62. In the example shown, the set of process identifiers 64 comprises six different process identifiers ("Process ID 1" to "Process ID 6"), each of which is a unique alphanumerical constant. Also recorded on the data carrier 54 are labels (not shown) associated with the process identifiers. For example, the process identifier "Process ID 1" may be associated with a label "Microdissection", or with a label "Archiving". Furthermore, in the present example, each of the data records 68, 70, 72 comprises a slice identifier identifying a slice of the object, and a process identifier selected from the set of process identifiers 64, the process identifier indicating a process to which the respective slice is intended to be subjected. For example, the data record 68 comprises the slice identifier "Slice ID 1" and the process identifier "Process ID 1", indicating that the physical slice identified by the slice identifier "Slice ID 1" is intended to be subjected to microdissection procedure. The slice identifier may also be indicated, e.g. in an alphanumerical form or as a barcode, on the physical slice itself, or on a slide, cartridge or other device carrying or containing the physical slice. Each of the data records 68, 70, and 72 further comprises a slice number corresponding to an order in which the respective slices were arranged before being cut from the object, e.g. from the paraffin block. For example, the numbers "Slice number 1", "Slice number 2", and "Slice number 3" could have the values three, four, and five, respectively, indicating that the slices identified, respectively, by the values of "Slice ID 1", "Slice ID 2", and "Slice ID 3", were adjacent and arranged in this order before they were cut from the paraffin block. The slice numbers "Slice number 1", "Slice number 2", and "Slice number 3" could also be integrated in the respective slice identifiers "Slice ID 1", "Slice ID 2", and "Slice ID 3".

Referring summarily to FIGS. 10 and 11, the PC 52, the monitor 60, the keyboard 58, and the mouse or trackball 56 provide a user interface that enables a user to select a data record, e.g. the data record 68, from the set of data records stored on the data carrier 54. The user interface may, for example, provide a menu on the monitor 60, allowing the user to indicate, for a selected physical slice, an intended use. The physical slice, e.g. the slice 12, is identified by a corresponding slice identifier. The intended use is identified by a corresponding process identifier.

The information processing device 62 thus enables the user to control or to manage a variety of processes involving one or more slices cut from the same object, e.g. from the same paraffin block, in particular for applications in the field of digital pathology and telepathology. For example, the user may indicate that a certain slice is intended to be archived and that another slice is intended to be used for microdissection.

Alternatively or additionally, the user may be enabled to select, for a selected first slice and for a selected second slice, a first staining method and a second staining method, respectively. The first staining method may be a staining method that is routinely used at a first laboratory, while the second staining method may be a staining method that is routinely used at second laboratory. By staining the first slice using the first staining method, staining the second slice using the second staining method, and comparing the two slices, a colour transformation may be determined. The colour transformation could be employed to transform the colours of a digital image of a slice taken at the first laboratory into colours that a familiar to a person, e.g. a pathologist, working at the second laboratory.

This invention can be used in particular for laser microdissection in a clinical pathology lab, or for standardization/transformation of colours associated with microscopy-related staining methods, in particular in combination with digital pathology and telepathology.

While the invention has been illustrated and described in detail in the drawings and in the foregoing description, the drawings and the description are to be considered exemplary and not restrictive. The invention is not limited to the disclosed embodiments. Equivalents, combinations, and modifications not described above may also be realized without departing from the scope of the invention.

The verb "to comprise" and its derivatives do not exclude the presence of other steps or elements in the matter the "comprise" refers to. The indefinite article "a" or "an" does not exclude a plurality of the subjects the article refers to. It is also noted that a single unit may provide the functions of several means mentioned in the claims. The mere fact that certain features are recited in mutually different dependent claims does not indicate that a combination of these features cannot be used to advantage. Any reference signs in the claims should not be construed as limiting the scope.

The invention claimed is:

1. A method for diagnosing biology, histology, and pathology of an object, the method comprising the acts of:
    providing the object comprising biological material and including a plurality of adjacent layers and a feature of interest extending through the plurality of adjacent layers;
    providing an image of a slice of a first of the plurality of the adjacent layers cut from the object;
    generating an image of a slice of a second of the plurality of adjacent layers cut from the object, a delay between cutting the slices of the first and second adjacent layers of the plurality of adjacent layers is selected from any of hours, days, weeks, months, years;
    determining a region of interest in the image of the slice of the second layer based on a region of interest in the image of the slice of the first layer;
    determining a region of interest in the slice of the second layer based on the region of interest in the image of the slice of the second layer; and extracting material from the region of interest in the slice of the second layer.

2. The method as set forth in claim 1, wherein the act of determining the region of interest in the image of the slice of the second layer comprises the acts of:
- determining a geometrical transformation which maps positions of features in the image of the slice of the first layer into positions of similar features in the image of the slice of the second layer; and
- applying the geometrical transformation to the region of interest in the image of the slice of the first layer.

3. The method as set forth in claim 1, wherein the act of determining the region of interest in the image of the slice of the second layer comprises the act of aligning the images of the slices of the first and second layers such that at least some features in the image of the slice of the first layer project onto similar features in the image of the slice of the second layer and/or such that a contrast of a superposition of the images of the slices of the first and the second layers is maximized.

4. The method as set forth in claim 1, further comprising the acts of:
- determining, based on the region of interest in the second image, a new position of a cutting tool relative to the slice of the second layer; and
- moving the cutting tool relative to the slice of the second layer to the new position.

5. The method as set forth in claim 4, wherein the act of determining the new position comprises the act of consulting at least one of a look-up table and evaluating a function for relating positions in the second image to one of positions of the cutting tool relative to the slice of the second layer and information equivalent to positions of the cutting tool relative to the slice of the second layer.

6. The method of claim 1, further comprising the acts of:
- storing a first slice identifier of the image of the first slice on a computer readable medium having records of a plurality of slice identifiers, each record including a slice identifier and a corresponding process identifier selected from a predefined set of process identifiers indicating a process to which respective slice identifier is to be subjected; and
- enabling a user, via a user interface, to select a record from the plurality of records.

7. The method of claim 6, wherein the plurality of records are identified by slice identifiers indicating an order in which the slices were arranged before being cut from the object.

8. An apparatus for use in diagnosing biology, histology, and pathology of an object comprising biological material having a plurality of adjacent layers and a feature of interest extending through the plurality of adjacent layers, comprising:
- a receiver configured to provide an image of a slice of a first of the plurality of the adjacent layers cut from the object;
- an imager configured to generate an image of a slice of the second layer of a second of the plurality of adjacent layers cut from the object; and
- a processor configured to:
  - determine a region of interest in the image of the slice of the second layer based on a region of interest in the image of the slice of the first layer, and
  - determine a region of interest in the slice of the second layer based on the region of interest in the image of the slice of the second layer; and
- an extractor configured to extract material from the region of interest in the slice of the second layer,
wherein the imager comprises a microscope objective and the extractor comprises a laser configured to generate a laser beam for transmittal to the slice of the second layer via the microscope objective,
wherein the extractor comprises a cutting tool configured to cut material out of the slice of the second layer, and the processor is further configured to:
- determine, based on the region of interest in the second image, a new position of the cutting tool relative to the slice of the second layer,
- move the cutting tool relative to the slice of the second layer to the new position, and
wherein the slice of the second layer is cut after a delay between cutting the slices of the first and second adjacent layers of the plurality of adjacent layers that is selected from any of hours, days, weeks, months, years.

9. A non-transitory computer readable medium comprising computer instructions which, when executed by a processor, configure the processor to perform the method for diagnosing biology, histology, and pathology of an object, the method comprising the acts of:
- providing the object comprising biological material and including a plurality of adjacent layers and a feature of interest extending through the plurality of adjacent layers;
- providing an image of a slice of a first of the plurality of the adjacent layers cut from the object;
- generating an image of a slice of a second of the plurality of adjacent layers cut from the object, a delay between cutting the slices of the first and second adjacent layers of the plurality of adjacent layers is selected from any of hours, days, weeks, months, years;
- determining a region of interest in the image of the slice of the second layer based on a region of interest in the image of the slice of the first layer;
- determining a region of interest in the slice of the second layer based on the region of interest in the image of the slice of the second layer; and
- extracting material from the region of interest in the slice of the second layer.

10. An information processing system, for use in biology, histology and pathology, configured for
- providing a predefined set of process identifiers;
- providing a set of data records associated with an object comprising biological material, the biological material including a plurality of adjacent layers and a feature of interest extending through the plurality of adjacent layers, wherein each of the data records comprises: two or more slice identifiers identifying, at least, a slice of a first of the plurality of the adjacent layers cut from the object and a slice of a second of the plurality of adjacent layers cut from the object, a delay between cutting the slices of the first and second adjacent layers of the plurality of adjacent layers having been selected from any of hours, days, weeks, months, years, a region of interest in the image of the slice of the second layer having been determined based on a region of interest in the image of the slice of the first layer, a region of interest in the slice of the second layer having been determined based on the region of interest in the image of the slice of the second layer, material from the region of interest having been extracted in the slice of the second layer,
- and a process identifier selected from the set of process identifiers, the process identifier indicating a process to which the slice is intended to be subjected; and
- providing a user interface for enabling a user to select a data record from the set of data records.

11. The information processing system as set forth in claim 10, wherein the set of process identifiers comprises a process identifier identifying a process selected from the following list of processes related to a slice:
- doing nothing with the slice;
- archiving the slice;
- disposing of the slice;
- generating an image of the slice;
- containing the slice in a microscope slide or cartridge;
- sending the slice to another laboratory;
- extracting material from the slice;
- freezing the slice;
- heating the slice;
- sealing the slice;
- marking a region of interest on the slice;
- staining the slice;
- staining the slice by a first staining method;
- staining the slice by a second staining method;
- defining a color transformation between two staining methods.

12. The information processing system as set forth in claim 10, wherein the set of data records indicates, for at least some of the slices indicated by the slice identifiers, an order corresponding to an order in which the at least some slices were arranged before being cut from the object.

13. The information processing system as set forth in claim 10, wherein the user interface is configured for enabling the user to modify the process identifier in the selected data record, by selecting another process identifier from the set of process identifiers.

14. The information processing system as set forth in claim 10, wherein a first data record in the set of data records comprises a first image or a first image identifier, the first image being a digital image of the slice identified by the slice identifier in the first data record.

15. The information processing system as set forth in claim 14, wherein the first data record comprises information indicating a region of interest in the first image, the region of interest having been defined by a user and the information having being recorded for being transferred to a laboratory in order to prepare a second slice of the object for microdissection.

16. The information processing system as set forth in claim 15, wherein the information processing system is configured for determining a region of interest to be cut from the second slice, by overlaying the first image and a digital second image of the second slice and projecting the region of interest defined in the first image onto the second image.

17. The information processing system as set forth in claim 10, wherein the user interface is configured for enabling the user to add a laboratory identifier selected from a set of laboratory identifiers to the selected data record, and to transmit the selected data record or selected components thereof to a laboratory identified by the selected laboratory identifier.

18. The information processing system as set forth in claim 10, wherein the user interface is configured for enabling the pathologist to ask a laboratory to cut two slices from an object comprising biological material and to generate digital images of the two slices.

* * * * *